United States Patent [19]
Santelli et al.

[11] Patent Number: 6,048,874
[45] Date of Patent: Apr. 11, 2000

[54] PARENTERAL METOLAZONE FORMULATIONS

[75] Inventors: Ronald J. Santelli, Rochester; Yu-Hsing Tu, Fairport, both of N.Y.

[73] Assignee: Medeva Pharmaceuticals Manufacturing, Inc., Rochester, N.Y.

[21] Appl. No.: 09/237,690

[22] Filed: Jan. 26, 1999

[51] Int. Cl.$^7$ ..................................................... A61K 31/47
[52] U.S. Cl. ............................................................ 514/312
[58] Field of Search .............................................. 514/312

[56] References Cited

U.S. PATENT DOCUMENTS

| | | |
|---|---|---|
| 4,472,380 | 9/1984 | Harris et al. . |
| 4,517,179 | 5/1985 | Raghunathan . |
| 4,522,818 | 6/1985 | Raghunathan . |
| 5,124,152 | 6/1992 | Biringer et al. . |
| 5,246,944 | 9/1993 | Greenlee et al. . |
| 5,633,240 | 5/1997 | Ranade . |
| 5,684,009 | 11/1997 | Ranade . |
| 5,814,623 | 9/1998 | Ranade . |

FOREIGN PATENT DOCUMENTS

| | | |
|---|---|---|
| WO 95/09625 | 4/1995 | WIPO . |
| WO 96/06615 | 3/1996 | WIPO . |

OTHER PUBLICATIONS

Belair, "the Renal Pharmacology of Metolazone, 2–Methyl–3–0–Tolyl–6–Sulfamyl–7–Chloro–1,2,3, 4–Tetrahydro–4–Quinazolinone," *Research Communications in Chemical Pathology and Pharmacology*, vol. 2, No. 1, pp. 98–117 (1971).

Bennett et al., "Comparison of Intravenous Chlorothiazide and Metolazone in Normal Man," *Current Therapeutic Research*, vol. 22, No. 2, pp. 326–334 (1977).

Cohen et al., "Physiological Disposition of a New Diuretic, $^{14}$C–Metolazone, in Dogs," *J. Pharmaceutical Sciences*, vol. 62, No. 6, pp. 931–936 (1973).

Grosskopf et al., "Combination of Furosemide and Metolazone in the Treatment of Severe Congestive Heart Failure," *Israel Journal of Medical Sciences*, vol. 22, No. 11 pp. 787–790 (1986).

*Primary Examiner*—James H. Reamer
*Attorney, Agent, or Firm*—Popovich & Wiles, P.A.

[57] ABSTRACT

The invention provides a method of making a pharmaceutical composition comprising a solution, which method comprises: (a) providing a solvent comprising propylene glycol, polyethylene glycol, polypropylene glycol, or glycerin; and (b) adding metolazone. The final concentration of metolazone in the solution is 9 mg/ml or more, the metolazone is not precipitated, and the concentration of metolazone is above its apparent equilibrium solubility. The invention also provides a pharmaceutical composition comprising a solution comprising: (a) a solvent other than water; and (b) 9 mg/ml or more of metolazone. The metolazone is not precipitated in this solution and the concentration of metolazone is above its apparent equilibrium solubility.

42 Claims, No Drawings

PARENTERAL METOLAZONE FORMULATIONS

FIELD OF THE INVENTION

This invention relates to parenteral formulations of metolazone, a diuretic.

BACKGROUND OF THE INVENTION

Metolazone, 7-chloro-1,2,3,4-tetrahydro-2-methyl-3-(2-methylphenyl)-4-oxo-6-quinazolinesulfonamide, is a potent antihypertensive and diuretic drug. Metolazone is a diuretic structurally related to quinethazone but has a greater potency, on a weight basis, than either quinethazone or hydrochlorothiazide. Metolazone is commonly available in oral dosage forms. Particularly in critical care situations such as for treatment of refractory edema or renal failure, a more desirable form of the drug is as an injectable solution. Aqueous solutions are preferred for intravenous administration, however, metolazone has very low solubility in water (about 0.02 mg/ml).

One approach to produce aqueous solutions of metolazone has been to increase the pH of the solution by the addition of, for example, alkali hydroxides. An aqueous solution having a pH of about 11 is sufficient to solubilize metolazone. However, such a high pH is undesirable for use in parenteral administration due to pain and irritation at the site of injection and possible precipitation of the metolazone. Moreover, metolazone is chemically unstable at this high pH. An example of using a high pH to solubilize metolazone is found in the work of Vasant Ranade (U.S. Pat. Nos. 5,633,240, 5,684,009, and 5,814,623). The highest concentration of metolazone achieved without precipitation was 2 mg/ml, and even this concentration usually resulted in precipitation. See Tables 1 and 2 of any of the Ranade patents. The preferred solutions in the Ranade patents contain about 1 mg/ml of metolazone. See U.S. Pat. No. 5,633,240 at column 2, lines 51 to 53.

Various other solutions to the problem of low metolazone solubility have been suggested in the art. Combining metolazone with other drugs to increase its effectiveness has been suggested. The formation of aqueous solutions containing various solvents and metolazone has also been reported. For example, aqueous metolazone solutions containing propylene glycol and ethyl alcohol have been produced in, for example, U.S. Pat. No. 5,124,152 (Biringer et al.). This patent exemplifies aqueous metolazone solutions having concentrations up to 4.25 mg/ml, and these solutions include some having a cosolvent of propylene glycol and ethyl alcohol. The '152 patent claims an aqueous metolazone solution having a concentration from 0.1 to 8 mg/ml of metolazone. The apparent equilibrium solubility limit of metolazone in an aqueous solution of 65% w/v propylene glycol, 15% w/v ethyl alcohol is approximately 8 mg/ml. See below. FIG. 1 of the '152 patent demonstrates that certain solutions can be formed using metolazone, ethyl alcohol, and propylene glycol. These solutions were formed by mixing the metolazone with the propylene glycol/ethyl alcohol mixture and then adding water. No heating was used. The metolazone in the solution shown in FIG. 1 of the '152 patent was above its apparent equilibrium solubility limit below about 2 mg/ml.

With some metolazone solutions containing organic solvents, there can be problems of irritation or precipitation of the drug at the site of injection. Thus, it is desirable to administer as low a total volume of the injectable solution as possible in order to minimize the side effects due to non-aqueous solvents. It is also desirable to prevent precipitation upon intravenous injection as it can result in reduced bioavailability of the drug, pain upon injection, or phlebitis.

Precipitation at the site of drug injection is related to the solubility of the drug in biological fluids. The rate of administration of a solution of a drug determines the degree of dilution in biological fluids and whether the solubility of the drug in the mixture of fluids will be exceeded. Normally one would expect that if the concentration of the drug at the site of injection exceeds the solubility of the drug in the biological fluid, precipitation would occur.

The present invention provides a method to make parenteral metolazone formulations in which the concentration of metolazone is much higher than any that have been previously proposed for parenteral formulations. In fact, the concentration of metolazone is above the apparent equilibrium solubility of metolazone in the solution. Because the concentration of metolazone is high, the amount of non-aqueous solvent per dose that must be introduced into the patient is lower than earlier formulations. Because less non-aqueous solvent is introduced into the patient, there should be less irritation at the site of injection. These solutions of metolazone also would be expected to not precipitate upon intravenous injection.

The method of making the parenteral metolazone formulations involves adding metolazone to a solvent other than water so that a high concentration of metolazone is dissolved in the solvent. In a preferred embodiment, the metolazone and solvent other than water are heated, the solution is cooled, and other solvents are added. The method results in solutions of metolazone that can remain stable for a long period of time. The solutions of the invention have much higher concentrations of metolazone than any previously reported solutions of metolazone that exceeded their apparent equilibrium solubility.

SUMMARY OF THE INVENTION

The invention provides a method of making a pharmaceutical composition comprising a solution, which method comprises: (a) providing a solvent comprising propylene glycol, polyethylene glycol, polypropylene glycol, or glycerin; and (b) adding metolazone. The final concentration of metolazone in the solution is 9 mg/ml or more, the metolazone is not precipitated, and the concentration of metolazone is above its apparent equilibrium solubility.

The invention provides a pharmaceutical composition comprising a solution comprising: (a) a solvent other than water; and (b) 9 mg/ml or more of metolazone. The metolazone is not precipitated in this solution and the concentration of metolazone is above its apparent equilibrium solubility.

It is to be understood that both the foregoing general description and the following detailed description are exemplary and explanatory and are intended to provide further explanation of the invention as claimed.

DESCRIPTION OF THE PREFERRED EMBODIMENTS

The invention provides a method of making a pharmaceutical composition comprising a solution, which method comprises: (a) providing a solvent comprising propylene glycol, polyethylene glycol, polypropylene glycol, or glycerin; and (b) adding metolazone. The final concentration of metolazone in the solution is 9 mg/ml or more, the metolazone is not precipitated, and the concentration of metolazone is above its apparent equilibrium solubility. In a preferred embodiment, the solvent comprises propylene glycol or polyethylene glycol. In another preferred embodiment, the solvent is propylene glycol.

In one embodiment, the solvent and metolazone mixture is heated. In other embodiments, the solvent and metolazone mixture is heated to a temperature in the range of 30 C to 90 C or to a temperature of 50 C. In another embodiment, the solvent and metolazone mixture is not heated.

The method can further comprise adding one or more additional solvents. These one or more additional solvents can be added after step (a) and before step (b) or added after step (b). The one or more additional solvents can be selected from water or ethyl alcohol.

In a preferred embodiment, the solvent is propylene glycol, and after step (b), the solvent and metolazone mixture is cooled and ethyl alcohol and water are added. This method can result in a solution comprising: (a) 9 to 15 mg/ml of metolazone; (b) 400 to 800 mg/ml of propylene glycol; (c) 50 to 250 mg/ml of ethyl alcohol; and (d)water. This method can result in a solution comprising: (a) 10 mg/ml of metolazone; (b) 650 mg/ml of propylene glycol; (c) 150 mg/ml of ethyl alcohol (95% v/v in water); and (d) water. This method can result in a solution consisting essentially of: (a) 10 mg/ml of metolazone; (b) 650 mg/ml of propylene glycol; (c) 150 mg/ml of ethyl alcohol (95% v/v in water); and (d) water.

In one embodiment of the general method described above, the solution comprises 9 to 15 mg/ml of metolazone. In another embodiment, the solution comprises 10 mg/ml or more of metolazone. The solution can further comprise a preservative. The pH of the solution can be from 4 to 10.5, or from 4 to 7.

The invention provides a pharmaceutical composition comprising a solution comprising: (a) a solvent other than water; and (b) 9 mg/ml or more of metolazone. The metolazone is not precipitated in this solution and the concentration of metolazone is above its apparent equilibrium solubility. In one embodiment, the solution comprises 9 to 15 mg/ml of metolazone. In other embodiments, the solution comprises 9.5 mg/ml or more of metolazone, 10 mg/ml or more of metolazone, or 12 mg/ml or more of metolazone.

The solution preferably comprises water. In one embodiment, the solvent comprises propylene glycol, polyethylene glycol, polypropylene glycol, or glycerin. In another embodiment, the solvent comprises propylene glycol or polyethylene glycol. In one embodiment, the solution comprises ethyl alcohol. In another embodiment, the solvent comprises propylene glycol and the solution comprises ethyl alcohol. In one embodiment, the weight ratio of ethyl alcohol to propylene glycol is from 1:20 to 1: 1. In another embodiment, the solvent comprises polyethylene glycol having an average molecular weight of from 200 to 800.

The solution can further comprise a preservative. The pH of the solution can be from 4 to 10.5, from 4 to 7, or from 4 to 5.

The solution can comprise: (a) 9 to 15 mg/ml of metolazone; (b) 400 to 800 mg/ml of propylene glycol; (c) 50 to 250 mg/ml of ethyl alcohol; and (d) water. The solution can consist essentially of: (a) 9 to 15 mg/ml of metolazone; (b) 400 to 800 mg/ml of propylene glycol; (c) 50 to 250 mg/ml of ethyl alcohol; and (d) water. The solution can comprise: (a) 10 mg/ml of metolazone; (b) 650 mg/ml of propylene glycol; (c) 150 mg/ml of ethyl alcohol (95% v/v in water); and (d) water. The solution can consist essentially of: (a) 10 mg/ml of metolazone; (b) 650 mg/ml of propylene glycol; (c) 150 mg/ml of ethyl alcohol (95% v/v in water); and (d) water.

The invention provides a method for treating a patient comprising administering parenterally an effective amount of a pharmaceutical composition described above.

The invention provides a stable solution of metolazone that is suitable for parenteral administration. The term parenteral is understood to include intravenous, intraarterial, and intracisternal. This invention therefore solves the problems of obtaining a maximum metolazone dosage in a minimum volume and of precipitation of the metolazone upon injection. The use of a concentrated solution (and thus a small volume of solution) avoids major side effects such as pain, vein necrosis, or drug precipitation at the site of injection.

In this invention, the solution can include organic solvents and solubilizers to produce solutions which are suitable to parenterally deliver to patients a high dose of metolazone in a relatively small volume of solution. In the method of this invention, metolazone is dissolved at high concentration in a suitable solvent at elevated temperature to form a stable solution in which the concentration of metolazone is above its apparent equilibrium solubility. Suitable solvents are described above and below.

The compositions of this invention can be prepared by first adding the metolazone to a glycol, preferably propylene glycol or polyethylene glycol. The solution is heated and stirred until the metolazone is dissolved. In a preferred embodiment, the metolazone is added to propylene glycol and this mixture is then heated to 50 C with stirring for a time sufficient to dissolve the metolazone. Alternatively, the metolazone can be added to a heated glycol. After sufficient mixing, water, ethyl alcohol, and any other desired ingredients can be added to prepare the composition for use in parenteral administration. Typically, the ethyl alcohol is 95% v/v in water, USP grade, and the water is sterile distilled water suitable for use in parenteral administration.

Suitable solvent mixtures for pharmaceutical formulations include aqueous mixtures with one or more of propylene glycol, ethyl alcohol, benzyl alcohol, polyethylene glycols, polypropylene glycol, or glycerin. The proportions vary depending upon desired drug solubility. Ethyl alcohol may be used as absolute alcohol or aqueous ethyl alcohol (95% v/v in water). Polyethylene glycol 300 and polyethylene glycol 400 often are preferred forms of polyethylene glycol.

Sterile compositions for use in intravenous administration are formulated according to conventional pharmaceutical practice. Water, ethyl alcohol, other solvents, or various other ingredients can be added to adjust the concentration and solution properties to a desired level. Buffers, preservatives, antioxidants, and the like can be incorporated as desired.

The solvent system added to the metolazone is selected to maximize the solubility of the metolazone and minimize the possibility of precipitation. Similarly, the proportions of solvent are selected to produce a biocompatible solution. Active ingredients other than metolazone can be present in the pharmaceutical composition and are added in such a manner that they form an effective solution for parenteral administration.

Example 1

This example illustrates the preparation of a stable solution of metolazone in an aqueous propylene glycol/ethyl alcohol solution.

Propylene glycol (3250.0 grams) was placed in a large beaker equipped with a stir bar. Fifty grams of metolazone was added with stirring, and the mixture was heated to 50 C and stirred until the metolazone was dissolved. The mixture was cooled to 25 C and 750.0 grams of ethyl alcohol (95% v/v in water) was added with stirring. This solution was diluted to a total volume of 5 liters by the addition of sterile, distilled water. The solution was stirred to complete mixing. The concentration of metolazone was 10 mg/ml.

The stability of a solution made by this method was determined as follows. The concentration of metolazone in a sample of the solution was determined by HPLC analysis to be 9.86 mg/ml. The sample had a pH of 6.93 and was clear. This sample was stored for one month at 40 C and evaluated again. The concentration of metolazone in the stored sample was determined by HPLC analysis to be 9.84 mg/ml. The stored sample had a pH of 7.30 and was clear.

Apparent Equilibrium Solubility of Metolazone

The apparent equilibrium solubility of metolazone in an aqueous solvent of 65% w/v propylene glycol/15% w/v ethyl alcohol (95% v/v in water) was determined as described below.

A 250 mg quantity of metolazone was equilibrated with 20 ml of a solvent consisting of 65% w/v propylene glycol, 15% w/v ethyl alcohol (95% v/v in water), and water for 24 hours at room temperature on a wrist action shaker. Amber glass was used throughout since metolazone has been reported to decompose when exposed to light. After equilibration, the solution was filtered through a 0.45 μm filter, diluted, and assayed spectrophotometrically at 346 nm. The apparent equilibrium solubility was determined to be 8.36 mg/ml using this method.

The apparent equilibrium solubility was redetermined more accurately as follows. A 300 g quantity of ethyl alcohol (95% v/v in water) and 1300 g of propylene glycol were added to a 2000 ml volumetric flask and mixed well. Next, purified water was added q.s. to 2000 ml. This is the solvent.

Nine 30 ml amber bottles were filled with 25 ml of the solvent and 400 mg of metolazone and mixed on a wrist arm shaker for 24 hours (3 bottles), 48 hours (3 bottles), and 72 hours (3 bottles). The samples were filtered through a membrane filter (Whatman 25 mm 601X Nylon Filter (0.45 μm)). The concentration of the samples was determined by HPLC and by UV analysis. The results are presented in Table 1 below.

TABLE 1

| Sample | Time Shaken | Concentration of Metolazone (mg/ml) | |
|---|---|---|---|
| | | HPLC | UV |
| 1 | 24 hrs | 7.90 | 8.09 |
| 2 | 24 hrs | 7.73 | 7.54 |
| 3 | 24 hrs | 7.65 | 7.41 |
| 4 | 48 hrs | 7.81 | 7.58 |
| 5 | 48 hrs | 7.68 | 7.56 |
| 6 | 48 hrs | 7.66 | 7.43 |
| 7 | 72 hrs | 7.61 | 7.30 |
| 8 | 72 hrs | 7.68 | 7.31 |
| 9 | 72 hrs | 7.91 | 7.55 |

The HPLC and UV analyses mentioned above were performed as follows.

HPLC Analysis

The sample concentrations were analyzed by an HPLC system (HP 1100, available from Hewlett-Packard, Palo Alto, Calif.) equipped with a $C_{18}$ column and an UV detector set at 230 nm. The mobile phase consisted of water and methanol at a ratio of 62/38 (v/v) and was used at a flow rate of 1.5 ml/minute.

UV Analysis

The sample concentrations were measured by the UV absorbance at 235 nm using an UV/VIS spectrophotometer (HP 8453, available from Hewlett-Packard, Palo Alto, Calif.).

The above description is provided for the purpose of describing embodiments of the invention and is not intended to limit the scope of the invention in any way. It will be apparent to those skilled in the art that various modifications and variations can be made without departing from the spirit or scope of the invention. Thus, it is intended that the present invention cover the modifications and variations of this invention provided they come within the scope of the appended claims and their equivalents.

What is claimed is:

1. A method of making a pharmaceutical composition comprising a solution, which method comprises:
    (a) providing a solvent comprising propylene glycol, polyethylene glycol, polypropylene glycol, or glycerin;
    (b) adding metolazone to the solvent; and
    (c) heating the solvent and metolazone mixture.

2. A method of making a pharmaceutical composition of claim 1, wherein the solvent comprises propylene glycol or polyethylene glycol.

3. A method of making a pharmaceutical composition of claim 1, wherein the solvent is propylene glycol.

4. A method of making a pharmaceutical composition of claim 1, wherein the solvent and metolazone mixture is heated to a temperature in the range of 30 C to 90 C.

5. A method of making a pharmaceutical composition of claim 1, wherein the solvent and metolazone mixture is heated to a temperature of 50 C.

6. A method of making a pharmaceutical composition of claim 1, further comprising adding one or more additional solvents.

7. A method of making a pharmaceutical composition of claim 6, wherein the one or more additional solvents are added after step (a) and before step (b).

8. A method of making a pharmaceutical composition of claim 6, wherein the one or more additional solvents are added after step (b).

9. A method of making a pharmaceutical composition of claim 6, wherein the one or more additional solvents are selected from water or ethyl alcohol.

10. A method of making a pharmaceutical composition of claim 1, wherein the solvent is propylene glycol, and after step (c), the solvent and metolazone mixture is cooled and ethyl alcohol and water are added.

11. A method of making a pharmaceutical composition of claim 10, wherein the solution comprises:
    (a) 9 to 15 mg/ml of metolazone;
    (b) 400 to 800 mg/ml of propylene glycol;
    (c) 50 to 250 mg/ml of ethyl alcohol; and
    (d) water.

12. A method of making a pharmaceutical composition of claim 10, wherein the solution comprises:
    (a) 10 mg/ml of metolazone;
    (b) 650 mg/ml of propylene glycol;
    (c) 150 mg/ml of ethyl alcohol (95% v/v in water); and
    (d) water.

13. A method of making a pharmaceutical composition of claim 10, wherein the solution consists essentially of:

(a) 10 mg/ml of metolazone;

(b) 650 mg/ml of propylene glycol;

(c) 150 mg/ml of ethyl alcohol (95% v/v in water); and (d) water.

14. A method of making a pharmaceutical composition of claim 1, wherein the solution comprises 9 to 15 mg/ml of metolazone.

15. A method of making a pharmaceutical composition of claim 1, wherein the solution comprises 10 mg/ml or more of metolazone.

16. A method of making a pharmaceutical composition of claim 1, wherein the solution further comprises a preservative.

17. A method of making a pharmaceutical composition of claim 1, wherein the pH of the solution is from 4 to 10.5.

18. A method of making a pharmaceutical composition of claim 1, wherein the pH of the solution is from 4 to 7.

19. A method of making a pharmaceutical composition of claim 1, wherein the final concentration of metolazone in the solution is 9 mg/ml or more, the metolazone is not precipitated, and the concentration of metolazone is above its apparent equilibrium solubility.

20. A method of making a pharmaceutical composition of claim 6, wherein the one or more additional solvents are added after step (c).

21. A method of making a pharmaceutical composition of claim 10, wherein the solution consists essentially of:

(a) 9 to 15 mg/ml of metolazone;

(b) 400 to 800 mg/ml of propylene glycol;

(c) 50 to 250 mg/ml of ethyl alcohol; and (d) water.

22. A method of making a pharmaceutical composition of claim 1, wherein the solution comprises 9.5 mg/ml or more of metolazone.

23. A method of making a pharmaceutical composition of claim 1, wherein the solution comprises 12 mg/ml or more of metolazone.

24. A method of making a pharmaceutical composition of claim 1, wherein the pH of the solution is from 4 to 5.

25. A method of making a pharmaceutical composition of claim 1, wherein the solvent comprises propylene glycol and the solution comprises ethyl alcohol.

26. A method of making a pharmaceutical composition of claim 25, wherein the weight ratio of ethyl alcohol to propylene glycol is from 1:20 to 1:1.

27. A method of making a pharmaceutical composition of claim 1, wherein the solvent comprises polyethylene glycol having an average molecular weight of from 200 to 800.

28. A pharmaceutical composition comprising a solution produced by the method of claim 1.

29. A pharmaceutical composition comprising a solution produced by the method of claim 11.

30. A pharmaceutical composition comprising a solution produced by the method of claim 12.

31. A pharmaceutical composition comprising a solution produced by the method of claim 13.

32. A pharmaceutical composition comprising a solution produced by the method of claim 21.

33. A method for treating a patient comprising administering parenterally an effective amount of a pharmaceutical composition of claim 28.

34. A method for treating a patient comprising administering parenterally an effective amount of a pharmaceutical composition of claim 29.

35. A method for treating a patient comprising administering parenterally an effective amount of a pharmaceutical composition of claim 30.

36. A method for treating a patient comprising administering parenterally an effective amount of a pharmaceutical composition of claim 31.

37. A method for treating a patient comprising administering parenterally an effective amount of a pharmaceutical composition of claim 32.

38. A method of making a pharmaceutical composition comprising a solution, which method comprises:

(a) providing propylene glycol;

(b) adding metolazone to the propylene glycol;

(c) heating the propylene glycol and metolazone mixture;

(d) cooling the propylene glycol and metolazone mixture;

(e) adding ethyl alcohol to the propylene glycol and metolazone mixture; and (f) adding water to the propylene glycol, metolazone, and ethyl alcohol mixture.

39. A method of making a pharmaceutical composition of claim 38, wherein the solution comprises:

(a) 9 to 15 mg/ml of metolazone;

(b) 400 to 800 mg/ml of propylene glycol;

(c) 50 to 250 mg/ml of ethyl alcohol; and (d) water.

40. A method of making a pharmaceutical composition of claim 38, wherein the solution consists essentially of:

(a) 9 to 15 mg/ml of metolazone;

(b) 400 to 800 mg/ml of propylene glycol;

(c) 50 to 250 mg/ml of ethyl alcohol; and (d) water.

41. A method of making a pharmaceutical composition of claim 38, wherein the solution comprises:

(a) 10 mg/ml of metolazone;

(b) 650 mg/ml of propylene glycol;

(c) 150 mg/ml of ethyl alcohol (95% v/v in water); and (d) water.

42. A method of making a pharmaceutical composition of claim 38, wherein the solution consists essentially of:

(a) 10 mg/ml of metolazone;

(b) 650 mg/ml of propylene glycol;

(c) 150 mg/ml of ethyl alcohol (95% v/v in water); and (d) water.

* * * * *